US005716011A

United States Patent [19]
Barbier

[11] Patent Number: 5,716,011
[45] Date of Patent: Feb. 10, 1998

[54] PROCESS FOR DIFFUSING AN ODORIFEROUS SUBSTANCE

[75] Inventor: Jean-Paul Barbier, Forqueux, France

[73] Assignee: L'Air Liquide, Societe Anonyme Pour L'Etude et L'Exploitation des Procedes Georges Claude, Paris Cedex, France

[21] Appl. No.: 545,821

[22] PCT Filed: Apr. 5, 1995

[86] PCT No.: PCT/FR95/00430

§ 371 Date: Nov. 9, 1995

§ 102(e) Date: Nov. 9, 1995

[87] PCT Pub. No.: WO95/26757

PCT Pub. Date: Oct. 12, 1995

[30] Foreign Application Priority Data

Apr. 5, 1995 [FR] France ................... 94/03983

[51] Int. Cl.$^6$ .................................. A62C 5/02
[52] U.S. Cl. .............................. 239/8; 116/214
[58] Field of Search ................ 239/8; 222/1, 3; 116/214, 206; 73/40.7

[56] References Cited

U.S. PATENT DOCUMENTS

| 2,322,617 | 6/1943 | Dayhuff | 222/3 |
| 2,468,369 | 4/1949 | Jones | 116/214 |
| 2,816,419 | 12/1957 | Mueller | 222/3 |
| 3,744,718 | 7/1973 | Morley | 239/8 |
| 3,950,960 | 4/1976 | Kawam | 222/3 |
| 3,956,923 | 5/1976 | Young et al. | 73/40.7 |
| 4,487,613 | 12/1984 | Yoshida et al. | 116/214 |
| 4,603,030 | 7/1986 | McCarthy | 422/4 |
| 4,698,620 | 10/1987 | Marshall | 116/214 |
| 4,734,371 | 3/1988 | Schmolke et al. | 222/3 |
| 4,984,450 | 1/1991 | Büger | 73/40.7 |
| 5,325,708 | 7/1994 | De Simon | 73/40.7 |
| 5,373,729 | 12/1994 | Seigeot | 73/40.7 |
| 5,386,717 | 2/1995 | Toda | 73/40.7 |
| 5,552,088 | 9/1996 | Pottier et al. | 116/214 |

FOREIGN PATENT DOCUMENTS

| 1 139 507 | 6/1989 | Japan . |
| WO 89/03227 | 4/1989 | WIPO . |

*Primary Examiner*—Andres Kashnikow
*Assistant Examiner*—Lisa Ann Douglas
*Attorney, Agent, or Firm*—Young & Thompson

[57] ABSTRACT

A process for diffusing an odoriferous substance placed in a container, as well as a gas mixture comprising an odoriferous substance in gas form and an odorless and breathable gas, placed in a container under a pressure higher than or equal to 5 bars.

18 Claims, No Drawings

PROCESS FOR DIFFUSING AN ODORIFEROUS SUBSTANCE

FIELD OF THE INVENTION

The present invention has as an object a process for diffusing an odoriferous substance, such as a perfume, as well as a gaseous mixture comprising an odoriferous substance in gas form, and an odorless and breathable gas.

BACKGROUND OF THE INVENTION

Different usual processes are known for diffusing an odoriferous substance. Among these processes, there may be mentioned, for example, those using a mixture consisting of an odoriferous substance in solid or liquid form, which is dissolved in a liquid solvent. Diffusing this mixture in air enables the diffusion of the odoriferous substance. Such a process may be carried out, for example, by means of an aerosol can when the solvent is sufficiently volatile or by bringing the solution in which said odoriferous substance is dissolved, to boiling. This diffusing may be assisted by carrying solvent vapors with air currents. The latter may be natural or, for a more important diffusion, be artificially created, for example by means of a ventilation system.

Diffusing of an odoriferous substance may for example be intended for masking an unpleasant odor or to spread a pleasant odor or a fragrance. Basically, odoriferous substances have been used in order to reinforce natural odors for a marketing purpose or for helping sales. It has been proposed to diffuse in the vicinity of stalls, for example a bakery or a grocery, odoriferous substances which produce an odor of brioche, fresh bread or fruits. In this case, the diffusing of odoriferous substances is mainly intended at attracting clients.

However, the usual processes, mentioned above, intended for diffusing odoriferous substances are disadvantageous if it is intended to diffuse odoriferous substances at an important distance from their source. As a matter of fact, costly means which are difficult to handle, for example ventilators, must be used.

SUMMARY OF THE INVENTION

The present invention has as an object a process for diffusing odoriferous substances which use is simplified, requires no costly means and in addition enables to diffuse said substances at constant amounts in well defined zones.

The invention then consists in a process for diffusing an odoriferous substance characterized in that:

a) a pressurized gas mixture under at least 5 bar is placed in a container, said gas mixture comprising the odoriferous substance in gas form and at least one odorless and breathable gas, b) the container is connected to a means for releasing the gas mixture outside said container in a controlled manner, and c) the gas mixture is released in a controlled manner outside the container so as to permit the diffusing of the odoriferous substance in gas form.

DETAILED DESCRIPTION OF THE INVENTION

The container is usually a glass bottle, preferably a compressed gas bottle. The means enabling to release said gas mixture in a controlled manner may for example consist of a pressure reducer or a flow regulator including a valve and a flow meter.

The gas mixture released outside the container, may, first diffuse in a duct or a network of ducts, and, secondly, in free air. The ducts may for example be normal rubber tubes of small diameter. As a result of the pressure to which it is subjected, said mixture may diffuse away from the container containing it. On the other hand, said ducts may be used as a means to cause diffusion of the odoriferous substance in a well localized zone. As a result, it is possible to consume only a small quantity of said mixture to produce the selected odor in a defined location.

According to another aspect of the invention, the gas mixture may first diffuse in an enclosure, such as a storing vat or a duct, containing a third gas, and this third gas may later be released outside the enclosure to be lead towards a utilization station or to be diffused in free air.

The third gas present in the enclosure enables to dilute the gas mixture released outside the container.

The third gas may be any gas, which is odorless or barely odoriferous, and to which an odor is intended to be conferred. Preferably, this third gas is a breathable gas such as defined hereinafter and more preferably, this third gas is oxygen or oxygen enriched air, for example enriched air at more than 25% molar oxygen.

Such an oxygen enriched gas should, in some applications, be capable of being rapidly detected in order to prevent incidents associated with an escape of this third gas outside the enclosure in which it is present.

An overoxygenation of a zone or of a medium may indeed cause an activation of combustion phenomena, resulting in a degradation of some materials such as electrical motors.

The process according to the invention enables to cause a diffusion of the odoriferous substance in the third gas, which is rapid, homogenous and simple, without substantially altering the composition.

Within the frame work of the present invention the term "breathable gas" means a gas or an association of gases which may be breathed by man or a mammal under conditions such that his health is not endangered.

The odorless and breathable gas according to the invention is preferably also non harmful, non toxic, non corrosive and non flammable. Moreover, it advantageously presents little or no risk to the environment. This is why air constitutes a particularly preferred breathable gas according to the invention.

In addition to air, oxygen or an association of gases comprising air and/or oxygen and a gas such as nitrogen, argon, helium or nitrogen protoxide may also be used as odorless and breathable gas.

The odoriferous substance according to the invention may be a perfume or any other substance giving a fragrance. Such substances are for example described in "Cosmetics, Fragrances and Flavors" of Louis Appell, Novox Inc. Publisher, Whiting, N.J. 08759, pp 231–256, which is incorporated in the present description by reference.

The odoriferous substance may also be malodorous, in order to produce an offensive odor. In this case, the gas mixture is essentially intended to diffuse in a third gas in order to confer an odor to the latter, for example to permit detection of leaks. As malodorous substance, $H_2S$ or organic sulfur compounds such as dimethyl sulfide may be mentioned.

The concentration of the odoriferous gaseous substance in said gas mixture should preferably be higher or much higher than its minimum threshold of olfactive perception in air θ'. This minimum threshold of perception may be determined according to the method described in "Cosmetics, Fragrances and Flavors", mentioned above. According to this method, the minimum threshold of perception of the substance in air θ', expressed in microgram per liter of air, is determined by means of the following formula:

$$\theta' = 5.4\, M \times 10^{-5} \times \theta \times P$$

in which:

M represents the molar mass of the odoriferous substance

θ represents the minimum concentration of the odoriferous substance in water for which there is an olfactive detection (in ppm, i.e., in part per million expressed in mass)

P is the vapor tension at 25° C. (expressed in mm of mercury) of the odoriferous substance The value θ is determined by a panel of persons which are trained in olfactive detection.

Normally, an odoriferous substance which can be used in said mixture has a threshold of perception in air between 0.001 and 10 ppb vol., generally between 0.01 and 1 ppb (1 ppb vol.=one part per billion in volume, or one part for $10^9$ in volume). The concentration of the odoriferous gas substance in said gas mixture may be higher than 0.01 ppm vol. (1 ppm vol.=one part per million by volume), and, preferably, lower than the threshold of flammability. Thus, the concentration in said odoriferous substance may be lower than 2% by volume when the gas mixture is under a pressure of 80 bar, or lower than 1% by volume under a pressure of 200 bar.

When the gas mixture is intended to diffuse in a third gas in order to give to the latter an odor as indicated above, concentration of the odoriferous substance in the gas mixture is advantageously selected so that the concentration of said odoriferous substance in the third gas is between 0.1 and 5 ppm vol., preferably between 2.5 and 5 ppm vol. These concentrations are more particularly used when the odoriferous substance is malodorous.

When the odoriferous substance is intended to diffuse in free air, before or after having diffused in one or more ducts, its concentration in the gas mixture is generally between 0.01 and 1000 ppm vol., more generally between 0.1 and 100 ppm vol.

Notwithstanding the embodiment of the invention, it is important, generally, that the content of odoriferous substance released in the air be lower than its threshold of toxicity (average value of exposure during 8 hours/day and 5 days/week).

By way of example, odoriferous substances and the fragrances that they produce, which are suitable according to the present invention, are mentioned in table I below.

TABLE I

| Odor | Odoriferous substance | Molar mass (M) | Vapor pressure at 25° C. P (mm Hg) | Minimum concentration θ of the substance in water for which there is olfactive detection (ppm) | Minimum threshold perception of the substance in air: θ | |
|---|---|---|---|---|---|---|
| | | | | | in microgram per liter of air | in ppb vol. |
| Lemon | Citral | 152 | 0.05 | 1 | $4.1.10^{-4}$ | 0.06 |
| Banana | Isoamyl acetate | 130 | 5.6 | 0.1 | $3.9.10^{-3}$ | 0.6 |
| Rose | Phenylethyl alcohol | 122 | 0.054 | 1 | $3.5.10^{-4}$ | 0.06 |
| Strawberry | Ethylmethyl-phenylglycidate | 206 | 0.03 | 0.001 | $3.3.10^{-8}$ | $3.6.10^{-6}$ |
| Jasmin | Benzyl acetate | 150 | 0.120 | 1 | $9.7.10^{-4}$ | 0.15 |

The gas mixture according to the invention may be pressurized in the container where it is present at a pressure between 50 and 200 bar, preferably between 100 and 200 bar.

The gas mixture comprising the odoriferous substance in gas form and at least one odorless and breathable gas, may be prepared by any known means for manufacturing gas mixture in which at least one of the components is present in an amount higher than the amount of at least another component.

A process of this type may for example consist in introducing a large excess of the odoriferous substance in the container, then pressurizing the latter with the odorless and breathable gas. The vapor pressure of the odoriferous substance will then be mixed with the odorless and breathable gas to constitute said gas mixture, which may then be released outside the container. The gas mixture thus obtained, permits the diffusion of the odoriferous substance in an amount which increases with time. As a matter of fact, as the gas mixture is released outside the container, the partial pressure of odorless and breathable gas in the container decreases while that of the odoriferous substance remains constant since it has been introduced in large excess.

According to another process, said mixture is formed by means of a given quantity of an odoriferous substance. This quantity may be selected so that said mixture, when it is released outside the container, provides a concentration, and therefore a smell which are substantially constant and predetermined notwithstanding the pressure of said mixture in the container. The odoriferous substance is introduced before, during, or after said odorless and breathable gas.

In order to maintain a constant concentration of the odoriferous substance in the container, it is however preferable to use a gas which is odorless and breathable and from which the water that it may contain has been removed, and to treat the internal wall of the container in order to substantially eliminate any phenomenon of surface adsorption. To do this, the odorless and breathable gas may be dried;

alternately, or in addition, it is also possible to clean the internal wall of the container to substantially eliminate all organic material such as fat, oil or hydrocarbon, after which this wall is dried, preferably under vacuum, to substantially eliminate any remaining trace of compound such as water, which can adsorb the odoriferous substance.

This treatment of the internal wall may, of course, also be carried out according to the first process described above in which a large excess of the odoriferous substance is introduced into the container.

According to another aspect the invention concerns a gas mixture comprising an odoriferous substance, such as mentioned above, and an odorless and breathable gas such as air or a combination of breathable gas such as defined above, this gas mixture being placed in a container under a pressure higher than or equal to 5 bar, preferably between 100 and 200 bar.

Advantageously, the internal wall of the container is pretreated in the manner indicated above, in order to limit or substantially eliminate the phenomenon of surface adsorption of the odoriferous substance. Such a pretreatment may consist in a cleaning followed by a careful drying, preferably under vacuum, of the internal wall.

The examples which follow aim at illustrating the present invention.

EXAMPLE 1

Gas mixture for diffusing an odor of banana at a given concentration

By means of a syringe, there are injected in a bottle having a capacity of 50 liters, previously cleaned and heated under vacuum, 2 grams of isoamyl acetate from which the vapor pressure at 25° C. is 5.6 mm mercury (746 Pa). Then, dry air is introduced, having a water content lower than 5 ppm vol., until reaching a pressure of 200 bar. There is thus obtained a composition containing 36 ppm vol. isoamyl acetate in air.

Isoamyl acetate is a substance which gives a banana odor with a threshold perception of 0.6 ppb.vol. calculated according to the method described by Louis Appell in "Cosmetic, Fragrance and Flavors", Novox Inc. Publisher Whiting, N.J. 08759, pp. 231-256. The concentration of isoamyl acetate in the composition is therefore 60,000 times higher than its threshold of perception, which enables to easily detect the odor of banana by diffusion of this mixture.

EXAMPLE 2

Gas mixture for diffusing an odor of banana at increasing concentrations when the pressure in the container containing it decreases By means of a syringe, in a bottle having a capacity of 50 liters previously cleaned and heated under vacuum, there are introduced about 200 grams of isoamyl acetate. Then, air is introduced until reaching a pressure of 200 bar. There is thus obtained a composition comprising 36 ppm vol. isoamyl acetate in air at 200 bar. This concentration gradually increases as the bottle is flushed to reach about 0.7% volume, when the latter is under atmospheric pressure.

EXAMPLE 3

Gas mixture for diffusing a smell of rose at a given concentration

By means of a syringe, in a 50 liters container previously cleaned and heated under vacuum, there are injected 0.02 gram of phenylethyl alcohol whose vapor pressure at 25° C. is 0.054 mm of mercury (7.2 Pa). Then, very dry air is introduced (less than 1 ppm water) until a pressure of 200 bar is reached. There is thus formed a composition comprising 0.35 ppm vol. of phenylethyl alcohol in air.

Phenylethyl alcohol is a substance which gives an odor of rose with a threshold perception of 0.06 p.p.b. vol. calculated according to method described by Louis Appell in the same reference as the one mentioned previously. The concentration of phenylethyl alcohol in the composition is therefore nearly 6,000 times higher than its threshold of perception which enables to detect the smell of rose by diffusion of this mixture.

EXAMPLE 4

Gas mixture for diffusing an odor of rose at increasing concentrations when the pressure in the container in which it is present decreases By means of a syringe, in a bottle having a capacity of 50 liters, previously cleaned and heated under vacuum, there are injected more than 2 grams of phenylethyl alcohol. Then, air is introduced until a pressure of 200 bar is obtained. There is thus formed a composition comprising 0.35 ppm vol. of phenylethyl alcohol in air at 200 bar. This concentration gradually increases with the flushing of the bottle to reach up to 70 ppm vol. when the latter is under atmospheric pressure.

EXAMPLE 5

Diffusion of an odor of banana in air

The container containing the gas mixture such as prepared in Example 1 is placed in a room whose volume is 100 m$^3$, in which as an average there are simultaneously 5 persons and in which the renewal of air is 30 m$^3$ per hour and per person (as required by French regulation).

The container is provided with a pressure regulator, a flow regulator including a valve and a flowmeter, and a tube enabling to send the gas mixture at a selected location of the room.

The flowmeter is adjusted so that the concentration of the odoriferous substance in the room is 30 times higher than its threshold of perception, or 18 ppb vol. This concentration is maintained by controlling the flow at 75 l/h.

This flow may be maintained constant during about 133 hours.

I claim:

1. Process for diffusing an odoriferous substance, which comprises:

a) placing a gas mixture pressurized to a pressure ranging between about 50 bar and about 200 bar in a container, said gas mixture comprising the odoriferous substance in gas form and at least an odorless and breathable gas, said odoriferous substance in gas form in said gas mixture having a concentration which is higher than 0.01 ppm vol., and higher than its minimum threshold of olfactive perception in air θ', expressed in microgram per liter, and determined according to the following formula:

$$\theta' = 5.4 \, M \times 10^{-5} \times \theta \times P$$

wherein

M represents the molar mass of the odoriferous substance

θ represents the minimum concentration of the odoriferous substance in water for which there is an olfactive detection P is the vapor tension at 25° C. (expressed in mm of mercury) of the odoriferous substance, and θ is a value determined by a panel of persons trained in olfactive detection, b) connecting the container to a means for releasing, in a controlled manner, the gas mixture outside said container, and c) releasing said gas mixture in a controlled manner outside the container, so as to permit the diffusion of the odoriferous substance in gas form.

2. Process according to claim 1, wherein the container is a gas bottle.

3. Process according to claim 1, further comprising treating the internal wall of the container before placing said gas mixture in the container, so as to substantially remove phenomena of surface adsorption from the internal wall.

4. Process according to claim 1, wherein the gas mixture, released outside the container, first diffuses in a duct or a network of ducts, then, secondly in free air.

5. Process according to claim 1, wherein the gas mixture, released outside the container, diffuses directly in free air.

6. Process according to claim 1, wherein the gas mixture diffuses in an enclosure containing a third gas, and gives an odor to this third gas.

7. Process according to claim 1, wherein the odorless and breathable gas is also not harmful, non-corrosive and non-flammable.

8. Process according to claim 7, wherein the odorless and breathable gas is air.

9. Process according to claim 1, wherein the odoriferous substance is a substance producing a fragrance.

10. Process according to claim 1, wherein the odoriferous substance is a substance producing an unpleasant odor.

11. Process according to claim 1, wherein the gas mixture is pressurized at a pressure between 100 and 200 bar.

12. Process according to claim 1, wherein the concentration of the odoriferous substance in gas form in said gas mixture is between 0.01 ppm vol. and 2% per volume.

13. Process according to claim 12, wherein the concentration of the odoriferous substance in gas form in said gas mixture is between 0.1 and 100 ppm vol.

14. A gas mixture comprising an odoriferous substance in gas form, and an odorless and breathable gas, wherein said gas mixture is placed in a container under a pressure ranging between about 50 bar and 200 bar, said odoriferous substance, said odoriferous substance in gas form in said gas mixture having a concentration which is higher than 0.01 ppm vol., and higher than its minimum threshold of olfactive perception in air θ, expressed in microgram per liter, and determined according to the following formula:

$$\theta' = 5.4\, M \times 10^{-5} \times \theta \times P$$

wherein

M represents the molar mass of the odoriferous substance

θ represents the minimum concentration of the odoriferous substance in water for which there is an olfactive detection P is the vapor tension at 25° C. (expressed in mm of mercury) of the odoriferous substance, and θ is a value determined by a panel of persons trained in olfactive detection.

15. A gas mixture according to claim 14, wherein the gas mixture is placed in a container under a pressure ranging between 100 and 200 bar.

16. A gas mixture according to claim 14, wherein the internal wall of the container is pretreated so as to substantially remove phenomena of absorption of the odoriferous substance from the internal wall of the container.

17. A gas mixture according to claim 14, wherein the odorless and breathable gas is air.

18. Method of detecting a leak of a third gas contained in an enclosure, which comprises:

releasing the gas mixture of claim 14 inside the enclosure so as to permit diffusion of the gas mixture in the third gas, and thereby conferring an odor to the third gas; and detecting any leaks of the third gas outside the enclosure.

* * * * *